(12) United States Patent
Duffy et al.

(10) Patent No.: US 9,414,914 B2
(45) Date of Patent: Aug. 16, 2016

(54) CATHETER ASSEMBLY WITH VALVE CRIMPING ACCESSORIES

(75) Inventors: Niall Duffy, Ballygluinin (IE); Paul Mearns, Galway (IE); John Gallagher, Galway (IE); Noam Miller, Netanya (IL)

(73) Assignee: Medtronic Ventor Technologies Ltd., Minneapolis, MN (US)

( * ) Notice: Subject to any disclaimer, the term of this patent is extended or adjusted under 35 U.S.C. 154(b) by 1172 days.

(21) Appl. No.: 12/911,458

(22) Filed: Oct. 25, 2010

(65) Prior Publication Data

US 2011/0208296 A1      Aug. 25, 2011

Related U.S. Application Data

(60) Provisional application No. 61/307,731, filed on Feb. 24, 2010.

(51) Int. Cl.
| | |
|---|---|
| *A61F 2/06* | (2013.01) |
| *A61F 2/24* | (2006.01) |
| *A61F 2/95* | (2013.01) |

(52) U.S. Cl.
CPC .......... *A61F 2/2427* (2013.01); *A61F 2/95* (2013.01); *A61F 2002/9522* (2013.01); *Y10T 29/53996* (2015.01)

(58) Field of Classification Search
CPC ...... A61F 2002/9522; A61F 2/95; A61F 2/97
USPC .......................... 623/2.11, 1.23, 1.12; 29/282
See application file for complete search history.

(56) References Cited

U.S. PATENT DOCUMENTS

| | | | |
|---|---|---|---|
| 3,657,744 | A | 4/1972 | Ersek |
| 5,370,685 | A | 12/1994 | Stevens |

(Continued)

FOREIGN PATENT DOCUMENTS

| | | |
|---|---|---|
| EP | 0903122 | 3/1999 |
| EP | 0916318 | 5/1999 |

(Continued)

*Primary Examiner* — Gregory Anderson
*Assistant Examiner* — Christina Lauer

(57) ABSTRACT

Catheter assemblies including a handle assembly located on the proximal end of the catheter assembly and a distal tip assembly located on the distal end of the catheter assembly. A crimping funnel is slidably positioned along the catheter. The crimping funnel includes a distal end having a first diameter and a proximal end having a second diameter smaller than the first diameter. An axial split is formed in the proximal end. A first collar is provided encompassing a portion of the proximal end. The first collar is configured to hold the axial split in the proximal end together when the first collar is at a first axial location along the proximal end, and to allow the axial split in the proximal end to open when the first collar is at a second axial location along the proximal end, such that the crimping funnel can be removed from the catheter assembly. Various methods of retaining a prosthetic valve on the catheter assembly during the crimping process are described.

10 Claims, 24 Drawing Sheets

(56) References Cited

U.S. PATENT DOCUMENTS

| | | |
|---|---|---|
| 5,545,214 A | 8/1996 | Stevens |
| 5,810,873 A * | 9/1998 | Morales .................. 606/198 |
| 5,814,097 A | 9/1998 | Sterman et al. |
| 5,911,752 A | 6/1999 | Dustrude et al. |
| 6,167,605 B1 * | 1/2001 | Morales .................... 29/282 |
| 6,926,732 B2 * | 8/2005 | Derus et al. ............ 623/1.12 |
| 8,359,721 B2 * | 1/2013 | Melsheimer et al. ....... 29/238 |
| 2003/0225445 A1 | 12/2003 | Derus et al. |
| 2004/0199239 A1 * | 10/2004 | Austin et al. ............ 623/1.11 |
| 2008/0004688 A1 | 1/2008 | Spenser et al. |
| 2008/0234797 A1 | 9/2008 | Styre |
| 2009/0093876 A1 * | 4/2009 | Nitzan et al. ............ 623/2.11 |

FOREIGN PATENT DOCUMENTS

| | | |
|---|---|---|
| FR | 99 14462 | 11/1999 |
| WO | 93/01768 | 2/1993 |
| WO | 97/28807 | 8/1997 |
| WO | 2006/026371 | 3/2006 |
| WO | 2009/111241 | 9/2009 |
| WO | WO2010/096176 | 8/2010 |

\* cited by examiner

CATHETER ASSEMBLY WITH VALVE CRIMPING ACCESSORIES

CROSS REFERENCE TO RELATED APPLICATIONS

This application claims the benefit of provisional patent application No. 61/307,731, filed Feb. 24, 2010.

BACKGROUND

1. Field of the Invention

The present invention relates to catheter assemblies, crimping accessories, and methods of crimping prosthetic valves onto a catheter. More specifically, the present invention provides for catheters and crimping accessories that simplify the process of crimping a prosthetic valve to a catheter.

2. Background

Recently, minimally invasive approaches have been developed to facilitate catheter-based implantation of valve prostheses on the beating heart, intending to obviate the need for the use of classical sternotomy and cardiopulmonary bypass. For example, French Patent Application No. 99 14462 illustrates a technique and a device for the ablation of a deficient heart valve by percutaneous route, with a peripheral valvular approach. International Application (PCT) Nos. WO 93/01768 and WO 97/28807, as well as U.S. Pat. No. 5,814,097 to Sterman et al., U.S. Pat. No. 5,370,685 to Stevens, and U.S. Pat. No. 5,545,214 to Stevens illustrate techniques that are not very invasive as well as instruments for implementation of these techniques.

With regard to the positioning of a replacement heart valve, attaching a valve on a support with a structure in the form of a wire or network of wires, forming a frame, has been proposed. This frame can be contracted radially in such a way that it can be introduced into the body of the patient percutaneously by means of a catheter, and it can be deployed so as to be radially expanded once it is positioned at the desired target site. U.S. Pat. No. 3,657,744 to Ersek discloses a cylindrical, frame-supported, tri-leaflet tissue heart valve that can be delivered through a portion of the vasculature using an elongate tool. The frame is mounted onto the expansion tool prior to delivery to the target location where the frame and valve are expanded into place.

Current techniques for delivering prosthetic heart valves via a catheter include a transapical approach for aortic valve replacement, typically involving the use of an introducer port, i.e., a large-bore overtube, of a trocar. A crimped, framed valve prosthesis reversibly coupled to a delivery catheter is transcatheterally advanced toward the native valve, where it is either forcefully deployed using a balloon catheter, or, alternatively, passively deployed using a self-expandable system. Accurate positioning of the replacement valve in the native annulus is critical to the success of the implantation.

In order to prepare such valve prostheses for implantation, the valve prosthesis can be initially provided in an expanded or uncrimped condition, then crimped or compressed around the catheter until it is as close to the diameter of the catheter as possible. Various methods and devices are available for crimping the valve onto the catheter, which may include hand-held devices or tabletop devices, for example. These crimping devices can initially provide an opening that is large enough to accommodate a valve in its expanded condition and positioned over a desired section of a catheter. This valve can then be compressed by reconfiguring the opening of the crimping device in some way to uniformly decrease the size of the opening until the valve is compressed to a desired size.

However, crimping a prosthetic valve using known hand held or tabletop devices requires a user to assemble and position the crimping device over a separately acquired catheter, resulting in the possibility of user error. In addition, positioning a crimping device over a catheter assembly can be complicated, for example, where the catheter assembly has a distal tip with a diameter larger than the final crimped diameter of the valve. In such situations, the known crimping devices are difficult to position on and remove from the catheter body.

The present invention provides a catheter assembly and crimping accessories for crimping a valve onto the catheter assembly. Crimping accessories according to the present invention can be provided pre-loaded onto a catheter assembly, and can be easily removed from the catheter assembly after a prosthetic valve has been crimped onto the catheter assembly, particularly with reference to catheter assemblies with enlarged distal tips. The crimping accessories described herein can also be provided separately from a catheter assembly and later positioned over the catheter. The catheter assemblies and associated crimping accessories described herein simplify the process of crimping a prosthetic valve and improve the accuracy of positioning the prosthetic valve within a body channel.

BRIEF SUMMARY OF THE INVENTION

The catheter assemblies and crimping accessories and methods described herein seek to remedy one or more of the disadvantages of previous crimping methods by providing catheters and crimping accessories that simplify the process of crimping a prosthetic valve or stent to a catheter. The crimping accessories and methods described herein are particularly useful for crimping a prosthetic valve onto a catheter having a distal tip with a diameter larger than the final crimped diameter of the prosthetic valve. In one embodiment of the present invention, a catheter assembly includes a handle assembly located on the proximal end of the catheter assembly and a distal tip assembly located on the distal end of the catheter assembly. A crimping funnel is slidably positioned along the catheter. The crimping funnel includes a distal end having a first diameter and a proximal end having a second diameter smaller than the first diameter. An axial split is formed in the proximal end. A first collar is provided encompassing a portion of the proximal end. The first collar is configured to hold the axial split in the proximal end together when the first collar is at a first axial location along the proximal end, and to allow the axial split in the proximal end to open when the first collar is at a second axial location along the proximal end, such that the crimping funnel can be removed from the catheter assembly.

BRIEF DESCRIPTION OF THE FIGURES

The accompanying figures, which are incorporated herein, form part of the specification and illustrate embodiments of crimpers for prosthetic valves and methods of crimping prosthetic valves and stents for transcatheter delivery. Together with the description, the figures further serve to explain the principles of and to enable a person skilled in the relevant art(s) to make and use the prosthetic valve crimpers and methods of crimping prosthetic valves for transcatheter delivery described herein. In the drawings, like reference numbers indicate identical or functionally similar elements.

DETAILED DESCRIPTION OF THE INVENTION

The following detailed description of crimpers for prosthetic valves and methods of crimping prosthetic valves and stents for transcatheter delivery refers to the accompanying figures that illustrate exemplary embodiments. Other embodiments are possible. Modifications can be made to the embodiments described herein without departing from the spirit and scope of the present invention. Therefore, the following detailed description is not meant to be limiting. Further, it would be apparent to one of skill in the art that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented. For example, while the description provided is directed to crimpers for crimping and loading a prosthetic heart valve onto a catheter, the crimping accessories described herein should not be limited to crimping and loading of a prosthetic valve. One of skill in the art would readily understand how to incorporate the features and structures described herein into crimping accessories for other purposes. For example, features of the crimping accessories described herein can be incorporated into catheters intended for other types procedures, such as delivery of stents or valves to a variety of areas in the body.

Figure 1:
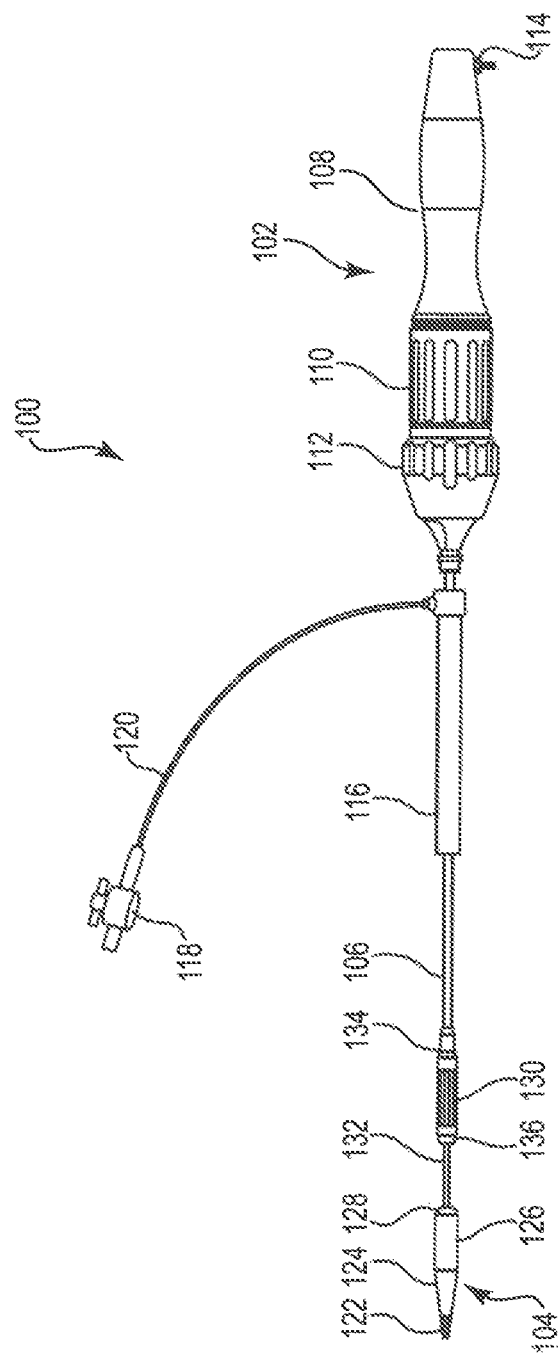
FIG. 1 illustrates a catheter assembly in accordance with one embodiment presented herein.

FIG. 1 illustrates a catheter assembly 100 in accordance with one embodiment presented herein. Catheter assembly 100 is depicted in FIG. 1 in a closed configuration. Catheter assembly 100 generally includes a handle assembly 102 located at the proximal end of the catheter, a distal tip assembly 104 located at the distal end of the catheter, and an introducer 116 slidably located along a outer delivery shaft 106 between the distal tip assembly 104 and the handle assembly 102.

Outer delivery shaft 106 is preferably a tubular flexible braided structure. Outer delivery shaft 106 can be formed of braided material fabricated from materials such as, but not limited to, polyethylene naphthalate (PEN), polyester (PET), stainless steel, titanium, nitinol, cobalt nickel alloy, polyamide, polyimide, or the like. In some embodiments, outer delivery shaft may contain reinforcing materials or structures. These structures can include an inner layer of polymer overlaid by a first reinforcing braid layer, overlaid by a coil reinforcement, finally overlaid with an outside layer of polymeric material. In another embodiment, the inner layer of polymeric material is overlaid by the coil reinforcement, which is overlaid by the braided reinforcement, which is finally overlaid with the outside layer of a polymeric material. In other embodiments, the inner layer of polymeric material is overlaid by a braided layer, which is overlaid by the coil winding, which is overlaid by another layer of braid, which is in turn overlaid by an outer polymeric layer. Preferably, however, any reinforcing layer used allows outer delivery shaft 106 to retain a degree of flexibility. Other flexible materials can also be used to form outer delivery shaft 106 consistent with embodiments of the present invention.

Handle assembly 102 includes a main handle 108, a proximal control knob 110, and a distal control knob 112. Main handle 108, a proximal control knob 110, and distal control knob 112 can be formed of any suitable material. For example, in some embodiments the handle and control knobs are formed of a polymer material. Other materials are possible, as would be understood in the art. A flushing port 114 can also be included on main handle 108. Flushing port 114 can be used to de-air the catheter assembly. Also, the native annulus is exposed to the blood pressure in a patient's cardiovascular system during use of a heart valve delivery catheter. As a consequence, in the absence of any counter pressure in this annulus, blood can flow inside towards the proximal end of the catheter, where it may coagulate and cause thrombosis. Thus, flushing port 114 can also allow fluid to be introduced into the native annulus to prevent such complications. In some embodiments, flush port 114 can also be used for site specific drug delivery or to introduce radiopaque fluid into the body.

As will be described herein, proximal control knob 110, and distal control knob 112 can be manipulated by a user in order to control operation of the distal tip assembly 104 of catheters described herein. Distal tip assembly 104 includes a tip 122, which is preferably slotted for the reasons described herein, a tip connector 124, and a support arm sleeve 126. A flushing tap 118 and a flushing tap lead 120 can be connected to an introducer 116. Introducer 116 is preferably a tubular member that is slidably located over outer delivery shaft 106. Introducer 116 may be formed of a variety of materials, for example, stainless steel or various polymer materials. Catheter 100 is configured to be advanced along a guide wire (not shown). Preferably, the catheter is advanced over a 0.035 inch guide wire. However, the dimensions of the catheter components can be adjusted for advancement over guide wires with larger or smaller diameters.

Catheter assembly 100 further includes a valve retaining sleeve 130, a valve retaining sleeve connector 134, a valve retainer 132, and a tip guard 128. Valve retaining sleeve connector 134 secures valve retaining sleeve 130 to the distal end of the outer delivery shaft 106. The outer delivery shaft 106 therefore extends from the interior of handle assembly 102 to sleeve connector 134. Slotted tip 122 and tip guard 128 are positioned on and connected to the distal end of an intermediate delivery shaft 132. Intermediate delivery shaft 132 extends from the interior of handle assembly 102 to slotted tip 122, to which the distal end of intermediate delivery shaft 132 is attached. Intermediate delivery shaft 132 is encompassed by outer delivery shaft 106 from the interior of handle assembly 102 until the outer delivery shaft 106 ends at sleeve connector 134. Tip guard 128 is attached to the proximal end of slotted tip 122. In one embodiment, tip guard 128 can be attached directly to intermediate shaft 132. Intermediate shaft 132 is preferably a tubular member.

It is understood that handle assembly 102 is merely an exemplary embodiment of a catheter handle that can he used in conjunction with the crimping devices and method described herein. The present invention is not limited to catheters having handles such as those described herein. The crimping devices and methods described herein can be used with catheter having different types of handles, including, e.g., conventional hand controlled catheter handles. It is further understood that other devices described with reference to FIG. 1, but not essential to the crimping devices and methods of the present invention, are optional and can be replaced with similar devices or can be left out entirely if not necessary for a particular application. For example, depending on the delivery method, catheters assemblies for use with the crimping devices and methods described herein can be provided without an introducer.

A guide wire shaft is encompassed within intermediate shaft 132 and extends from the inside of handle assembly 102 to the proximal end of slotted tip 122. Thus, in one embodiment of the present invention, at least three shafts extend from the main handle, and the shafts are nested along at least a part of their lengths. Specifically, guide wire shaft 504 is encompassed by the intermediate delivery shaft 132 from a position inside of handle assembly 102 to the interior of slotted tip 122, which is preferably hollow through at least a portion thereof. Intermediate delivery shaft 132 is connected to, and ends, at the proximal end of slotted tip 122. In turn, intermediate delivery shaft 132 is encompassed by the outer delivery shaft 106 from a position inside of handle assembly 102 to the valve retaining sleeve connector 134. Outer delivery shaft 106 is connected to, and ends, at the retaining sleeve connector 134. Intermediate shaft 132 and guide wire shaft 504 can be constructed of various polymer materials, and may be braided structures using materials described above with reference to outer delivery shaft 106.

Figure 2:
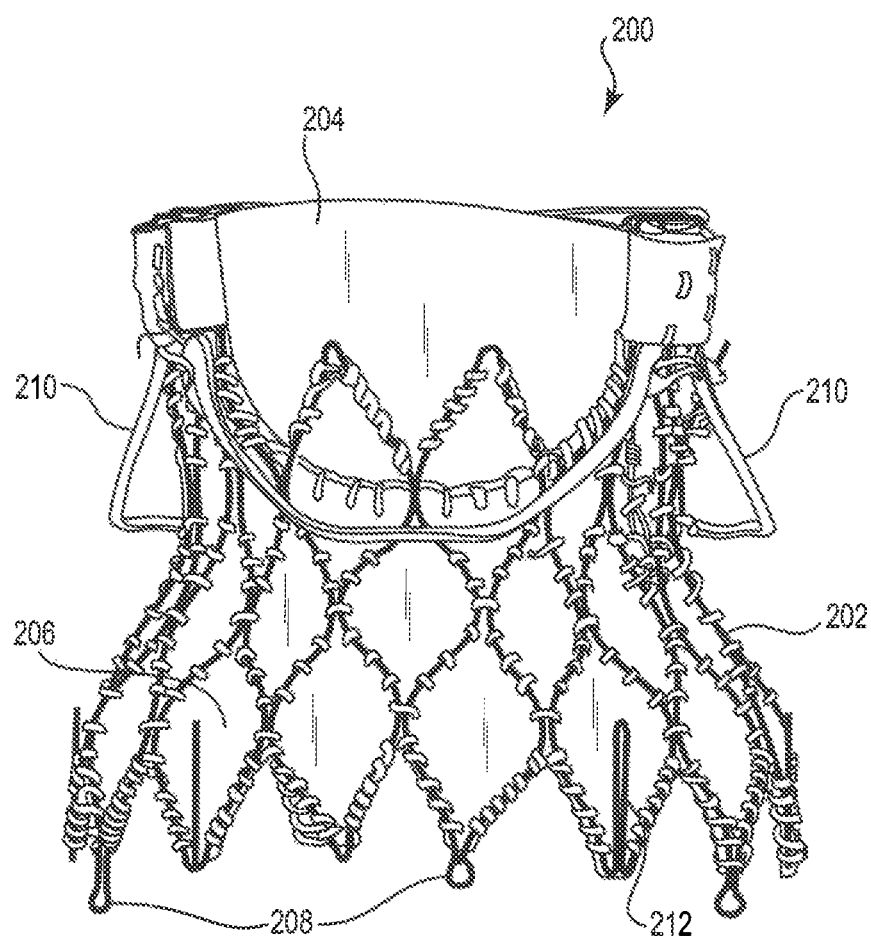
FIG. 2 is a depiction of one of the many types of prosthetic valves that are compatible with the valve crimping accessories described herein. The exemplary prosthetic valve is shown herein to facilitate explanation of the structure and operation of the crimping accessories and methods described herein.

FIG. 2 depicts an exemplary prosthetic heart valve 200. Heart valve 200 is illustrated herein in order to facilitate description of the crimping accessories according to embodiments of the present invention. It is understood that any number of alternate prosthetic heart valves can be used with the crimping accessories described herein. Prosthetic heart valve 200 is merely exemplary. Prosthetic heart valve 200 includes support frame 202, valve leaflets 204 located towards the distal end of support frame 202, valve skirt 206, and three fixation hooks 208 extending from the proximal end of valve support 208. Support frame 202 is preferably formed of a self-expanding material, e.g., nitinol. Other self-expanding or shape memory materials can be used instead of nitinol. Preferably, three valve leaflets 204 are provided to form a tricuspid valve structure within prosthetic heart valve 200. It is understood that alternate valve leaflet configurations, e.g., bicuspid valves, can be included in prosthetic heart valves for use in conjunction with the crimping devices and methods described herein. Leaflets 204 and skirt 206 are preferably formed of animal pericardium tissue, such as, e.g., bovine pericardium or porcine pericardium. In other embodiments, leaflets 204 and skirt 206 can be formed from synthetic materials. Leaflets 204 and skirt 206 are attached to support frame 202, preferably using sutures, as shown in FIG. 2. It is understood that various types of sutureless bonding methods can be used to attach leaflets 204 and skirt 206 to frame 202. Fixation hooks 208 extend from the proximal end of support frame 202 and include eyelets at their proximal end. Fixation hooks 208, which are optional can be formed in various configurations other than that shown. For example, fixation hooks 208 can be J shaped hooks or eyelets 208 can take on any number of sizes or shapes while remaining compatible with the crimping devices and methods described herein. Support frame 202 further includes three support arms 210, which are attached to support frame 202 towards its distal end. Alternately, support arms 210 can be formed integrally with support frame 202. Support arms 202 are preferably formed of a self-expanding material, e.g., nitinol. Other self-expanding or shape memory materials can be used instead of nitinol. Support arms 202 can be attached to support frame 202 such that they are biased away from support frame 202 but can pivot radially with respect to support frame 202. A plurality of barbs 212 can be provided on the proximal end of support frame 202. Barbs 212 extend for a distance towards the distal end of support frame 202. Preferably, barbs 212 extend in an approximately axial direction. Barbs 212, which are optional, can also be biased or curved slightly inward, but with less inward curve than the surrounding section of support frame 202. Because the distal end of barbs 212 define a greater diameter than the surround support frame, they receive the majority of forces when the proximal end of support frame 202 is crimped using the techniques described herein. This prevents damage to support frame 202 and, more particularly, to the sutures attached skirt 206 to support frame 202.

Figure 3:
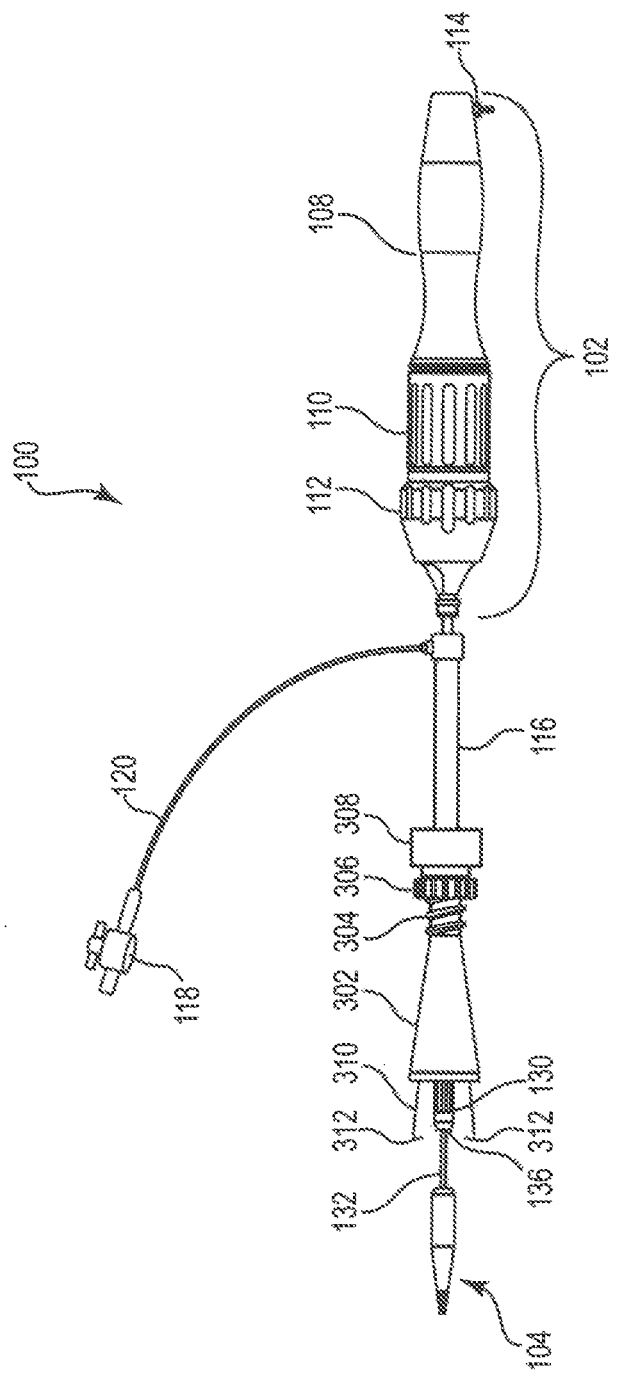
FIG. 3 illustrates the catheter assembly of FIG. 1 including accessories for crimping a prosthetic valve onto the catheter assembly.

FIG. 3 illustrates the catheter assembly 100 as shown in FIG. 1, further including accessories for crimping a prosthetic heart valve onto the catheter assembly. Specifically, FIG. 3 depicts catheter assembly 100 with a crimping funnel 302 loaded thereon. Crimping funnel 302 has a split proximal end 304. A funnel collar 306 is threaded around split proximal end 304 in order to hold split proximal end 304 together during the crimping process. Although FIG. 3 depicts funnel collar 306 secured to threads provided on the proximal end 304, it is understood that other methods could be used to removably secure a funnel collar to crimping funnel 302. For example, removable clips could be used to secure the funnel collars to crimping funnel 302. Alternately, sliding collars could be used. A wire loading ring 308 is initially positioned proximally to the crimping funnel 302. Crimping wires 310 are connected to wire loading ring 308 and extend distally through the funnel 302 and protrude from the distal end of funnel 302. Each crimping wire 310 has an eyelet hook 312 on the end thereof for securing the eyelets of a valve. For example, each eyelet 208 of prosthetic valve 200, shown in FIG. 2, can be connected to an eyelet hook 312 in order to a fix the valve 200 in position for crimping. Crimping accessories shown in FIG. 3 can be preloaded onto catheter assembly 100. It is understood that the crimping accessories shown in FIG. 3 can be used with a variety of existing catheter assemblies other than those shown in the figures of the present application. Crimping funnel 302, funnel collar 306, and wire loading ring 308 can be formed of a variety of materials. Preferably, the crimping funnel 302, funnel collar 306, and wire loading ring 308 are formed generally of a polymer material.

Figure 4:
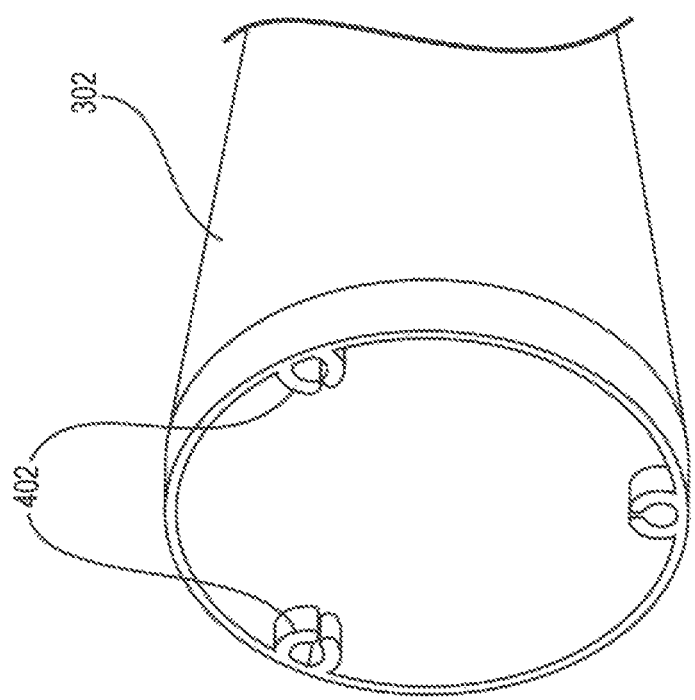
FIG. 4 is a detailed view of the distal end of a funnel according to one embodiment of the present invention.

FIG. 4 is a perspective view of the distal end of crimping funnel 302. As shown in FIG. 4, three clips 402 are provided on the inside of the proximal end of crimping funnel 302. When catheter assembly 100 with crimping accessories loaded thereon is in the configuration shown in FIG. 3, each clip 402 retains one of the crimping wires 310. Such a configuration holds the crimping wires at a desired circumferential position. In operation, a prosthetic valve, such as valve 200 shown in FIG. 2, is loaded onto catheter assembly 100 when funnel 302 and crimping wires 310 are generally in the position shown in FIG. 3. At this point eyelet hooks 312 are positioned distally of the valve retainer 136. Preferably, three crimping wires 310 are used. It is understood that more than three crimping wires can be provided, each corresponding to an eyelet 208 on a prosthetic valve to be loaded onto the catheter assembly 100. Wire loading ring 308 is preferably removably attached to introducer 116. As noted above, crimping wires 310 are connected wire loading ring 308. Therefore, when eyelet hooks 312 are positioned within eyelets 208, valve 200 can be held in a fixed axial position as funnel 302 is moved distally down the catheter assembly 100.

Figure 5:
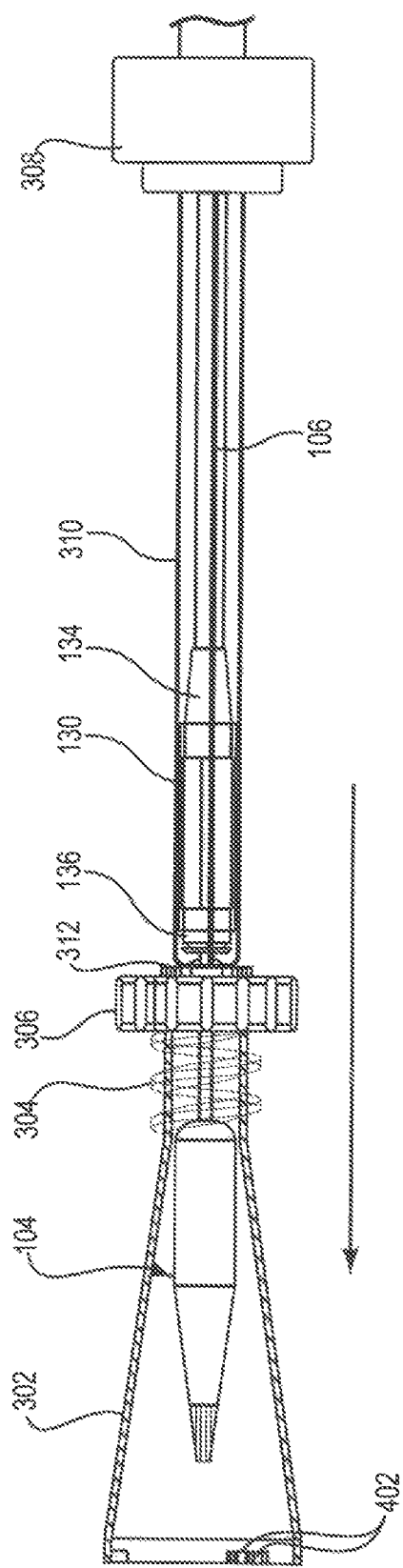
FIG. 5 illustrates a catheter assembly with crimping accessories in one stage of the crimping process. At this stage, the crimping funnel has been advanced over the prosthetic valve to crimp the valve.

FIG. 5 illustrates the distal end of catheter assembly 100 after crimping funnel 302 has been advanced distally down the catheter assembly. Because the prosthetic valve assembly 200 is held in place by the crimping wires 310 as funnel 302 is forced distally down the catheter assembly 100, the diameter of the prosthetic valve assembly 200 is gradually decreased until the valve 200 is crimped and positioned substantially within the split distal end 304 of crimping funnel 302. At this point the entire funnel 302 is positioned distally of valve retainer 136 and valve retaining sleeve 130. Eyelet hooks 312 of crimping wires 310 remain hooked in eyelets 208 of prosthetic valve assembly 200.

Figure 6:
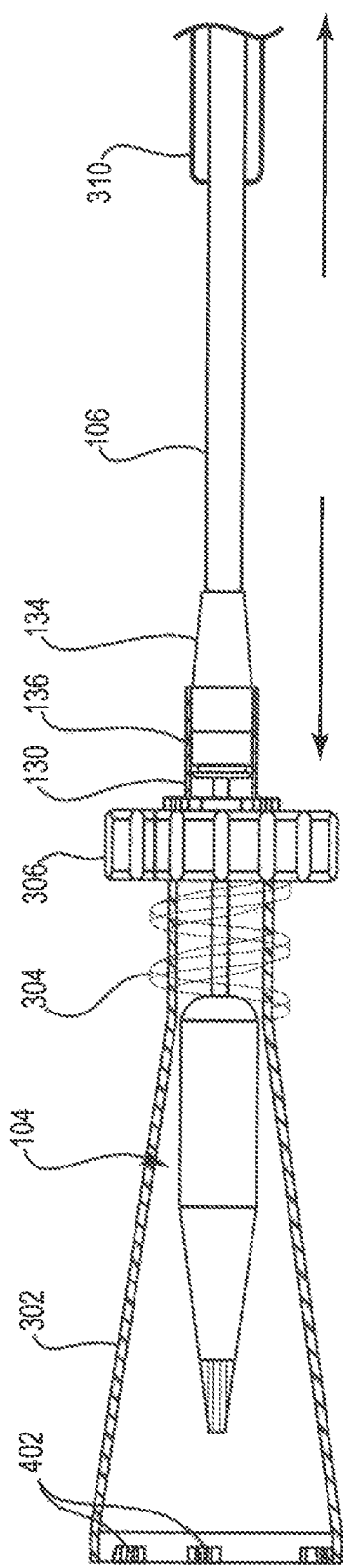
FIG. 6 illustrates the distal end of a catheter assembly with crimping accessories in another stage of the crimping process. At this stage, the wire crimping hooks have been removed from the prosthetic valve and the wire loading ring has been retracted.

Eyelet hooks 312 are then removed from eyelets 208 of the prosthetic valve 200. The wire loading ring 308 is then retracted proximately along the catheter assembly 100. At this point outer delivery shaft 106 can be advanced distally, thereby advancing valve retaining sleeve 130 over the crimped valve, as shown in FIG. 6. As valve retaining sleeve is advanced, its distal end primarily contacts barbs 212 of prosthetic valve assembly 200, thereby reducing friction that could be caused by the inner surface of valve retaining sleeve 130 sliding over support frame 202. This reduces damage to the support frame 202 and the sutures securing the valve skirt 206 to the support frame 200. It is understood that the crimping methods described herein can be used to crimp valves that do not have barbs provided thereon. Alternate methods can be used to prevent damage to support frame 202. For example, in other embodiments, skirt 206 can be bonded to the interior of frame 202, or the sutures securing the skirt to the frame can be secured to eyelets on the interior of frame 202 or passages can be provided in frame 202 such that the sutures are not exposed on the exterior of frame 202. In such embodiments, there is a reduced risk of damage to support frame 202 as the valve retaining sleeve 130 is advanced over the prosthetic valve assembly 200.

Figure 7:
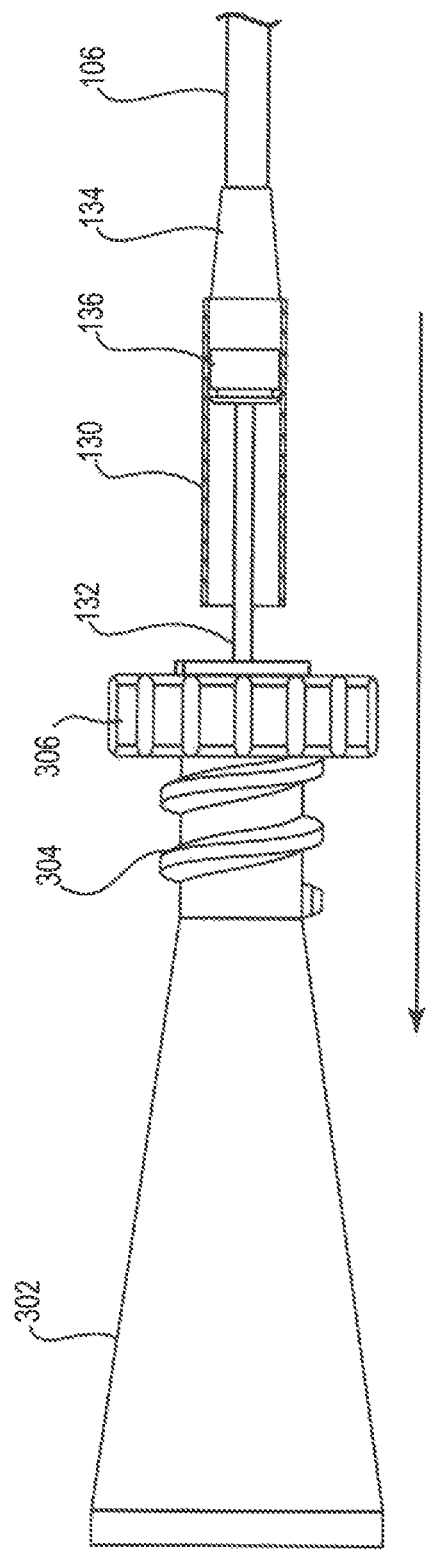
FIG. 7 illustrates the distal end of a catheter assembly with crimping accessories in another stage of the crimping process. At this stage, the crimping funnel has been removed from the valve.

As shown in FIG. 7, crimping funnel 302 is then advanced further distally, such that the distal end of valve assembly 200 is no longer encompassed by the split proximal end 304 of the crimping funnel 302. At this point the eyelets 208 of valve prosthesis 200 would be retained within valve retainer 136, as will be described in further detail with reference to FIGS. 17-18 and FIGS. 23-24. Furthermore, the proximal end of prosthetic valve assembly 200 is encompassed by valve retaining sleeve 130. The distal end of the prosthetic valve 200, including support arms 210, protrude from the distal end of valve retaining sleeve 130. At this position, support arms 210 are in the fully deployed position. Support arm sleeve 126 and the remainder of distal tip assembly 104 are encompassed by crimping funnel 302.

Figure 9:
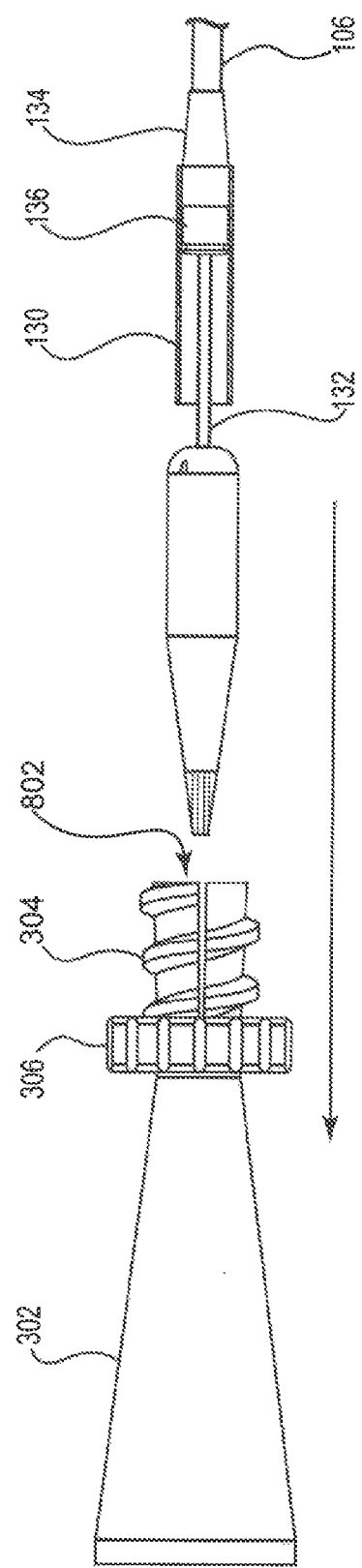
FIG. 9 illustrates the distal end of a catheter assembly with crimping accessories in another stage of the crimping process. At this stage, the funnel collar has been advanced over the distal tip of the catheter assembly.

Crimping funnel 302 is then removed from the catheter assembly by sliding it over distal tip assembly 104. Because the diameter of support arm sleeve 126 is approximately equal to or slightly larger than the diameter of split proximal end 304 of funnel 302 when funnel collar 306 is holding split proximal end 304 together, funnel collar 306 can be moved distally down the split proximal end 304 of the funnel 302 to allow the two halves of the split proximal end 304 to split apart, thereby increasing the diameter of the split proximal end 304 to a diameter greater than that of support arm sleeve 126. Funnel 302 can then be removed from the distal end of the catheter assembly 100, as shown in FIG. 9. At this point the distal end of prosthetic valve 200 is still protruding from the distal end of valve retaining sleeve 130.

Figure 10:
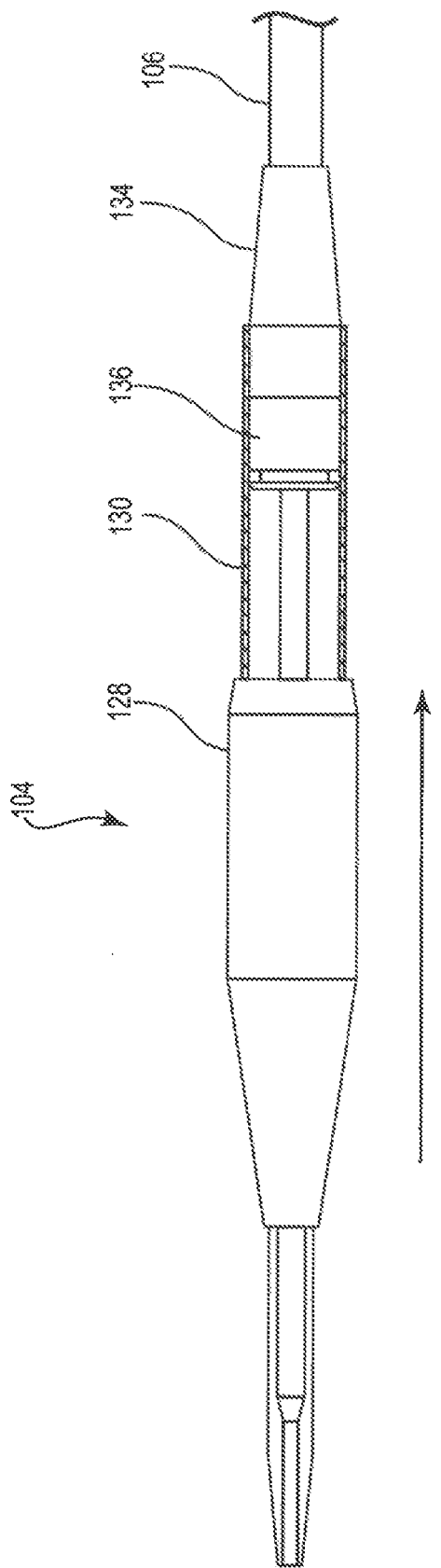
FIG. 10 illustrates the distal end of a catheter assembly with crimping accessories in another stage of the crimping process. At this stage, the support arm sleeve has been retracted to cover the distal end of the prosthetic valve.

In order to capture and crimp the distal end of prosthetic valve 200, support arm sleeve 126 is retracted proximally along the catheter 100 to reach the position shown in FIG. 10. The proximal end of the support arm sleeve 126 contacts the support arms 210 of prosthetic valve 200 thereby capturing the distal end of the prosthetic valve within support arm sleeve 126 as shown in FIG. 10. Because the inner surface of support arm sleeve 126 primarily contacts the supports arms 210, and not the main body of valve frame 202, damage to the valve frame 202 is reduced.

Figure 11:
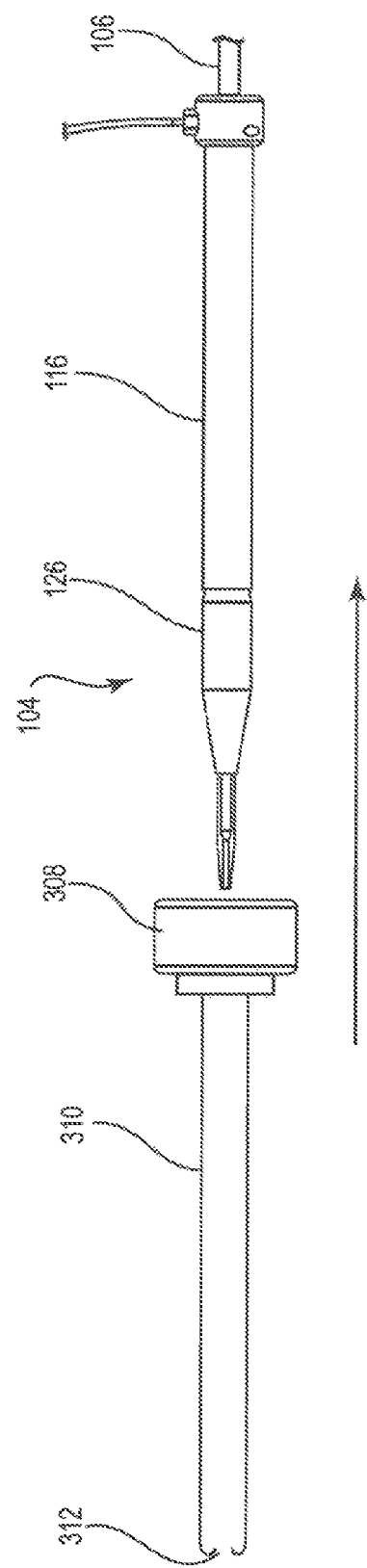
FIG. 11 illustrates the distal end of a catheter assembly with crimping accessories in another stage of the crimping process. At this stage, the wire loading ring has been removed from the catheter assembly and the introducer has been advanced.
Figure 12:
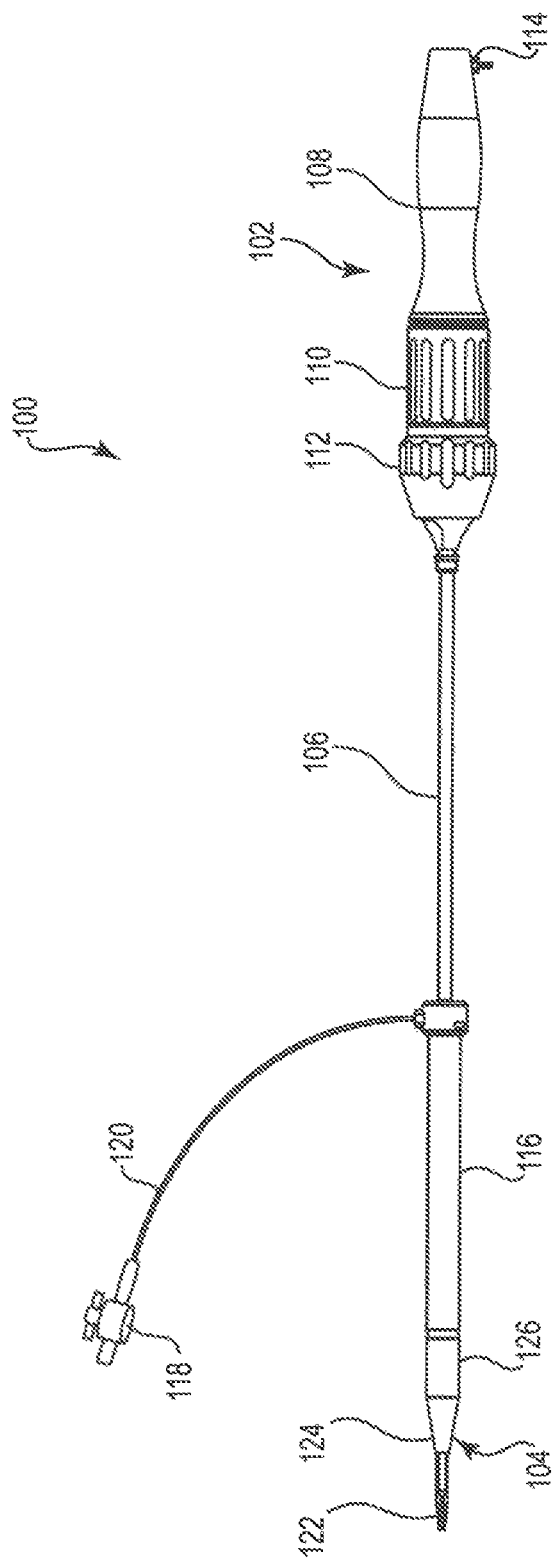
FIG. 12 illustrates a catheter assembly according to one embodiment of the present invention in a closed position after a prosthetic valve has been loaded onto the catheter.

As shown in FIG. 11, wire loading ring 308 can then be detached from introducer 116 and removed over the distal tip assembly 104. Introducer 116 can also be advanced distally to abut against the proximal end of support arm sleeve 126, thereby covering valve retaining sleeve 130. FIG. 12 shows catheter assembly 100 in a closed configuration with the prosthetic valve loaded therein. The catheter can then be used to deliver prosthetic valve assembly 200 to a desired location in a body.

Figure 8:
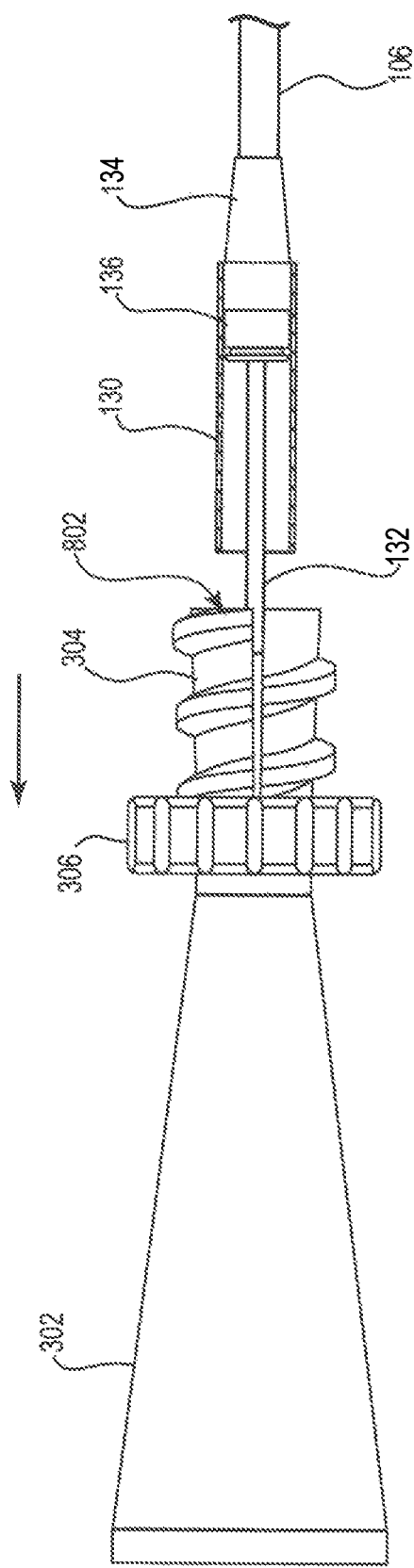
FIG. 8 illustrates the distal end of a catheter assembly with crimping accessories in another stage of the crimping process. At this stage, the funnel collar has been moved to allow the proximal end of the funnel to split, allowing the funnel to be removed over the device tip.
Figure 13:
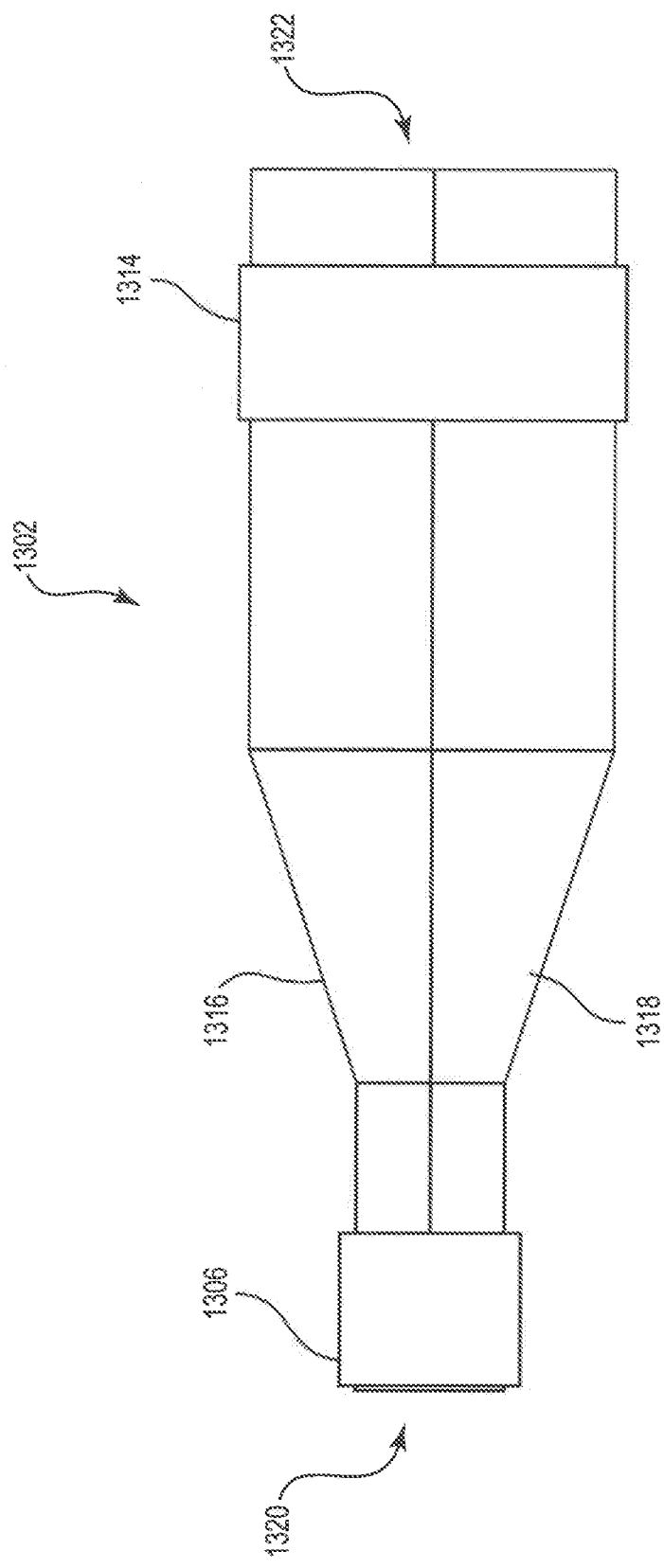
FIG. 13 illustrates an embodiment of a crimping funnel according to another embodiment of the present invention.

FIG. 13 shows another embodiment of a crimping funnel in accordance with the present invention. Crimping funnel 1302 has two halves 1316 and 1318, which are held together by two funnel collars, proximal collar 1306 and distal collar 1314. Proximal collar 1306 is located at the proximal end 1320 of funnel 1302 and distal collar 1314 is located at the distal end 1322 of funnel 1302. When used to crimp valve, funnel 1302 is placed on a catheter such that the smaller diameter proximal end 1320 is located proximally of the distal end 1322, in much the same configuration as funnel 302 shown in FIG. 3. Preferably, both the distal and proximal ends of crimping funnel 1302 are threaded on their exterior surface. The interior surfaces of collars 1306 and 1314 preferably have complimentary threads formed thereon. To allow the funnel 1302 to split into its two halves 1316 and 1318, such that the funnel is able to slide over distal tip assembly 104 as described above with reference to FIGS. 8-9, proximal funnel collar 1306 and distal funnel collar 1314 are removed from crimping funnel 1302. The crimping accessories can then be removed over the distal tip 104 of catheter assembly 100.

In another embodiment, crimping funnel 1302 can be provided with a gradually decreasing diameter, similar to funnel 302 described above. The funnel can be provided with sections on each end with a diameter larger than the diameter of the funnel surrounding those sections. Proximal collar 1306 and distal collar 1314 can be attached to the increased diameter sections. In such embodiments, proximal collar 1306 and distal collar 1314 be moved towards the center of the funnel instead of being removed over the ends of the funnel. Because proximal collar 1306 and distal collar 1314 have diameters greater than the sections of the funnel interior to the end sections, funnel 1302 can split, thereby reaching a greater diameter for removal over distal tip assembly 104, without removing collars 1306 and 1314 from the funnel.

Figure 14:
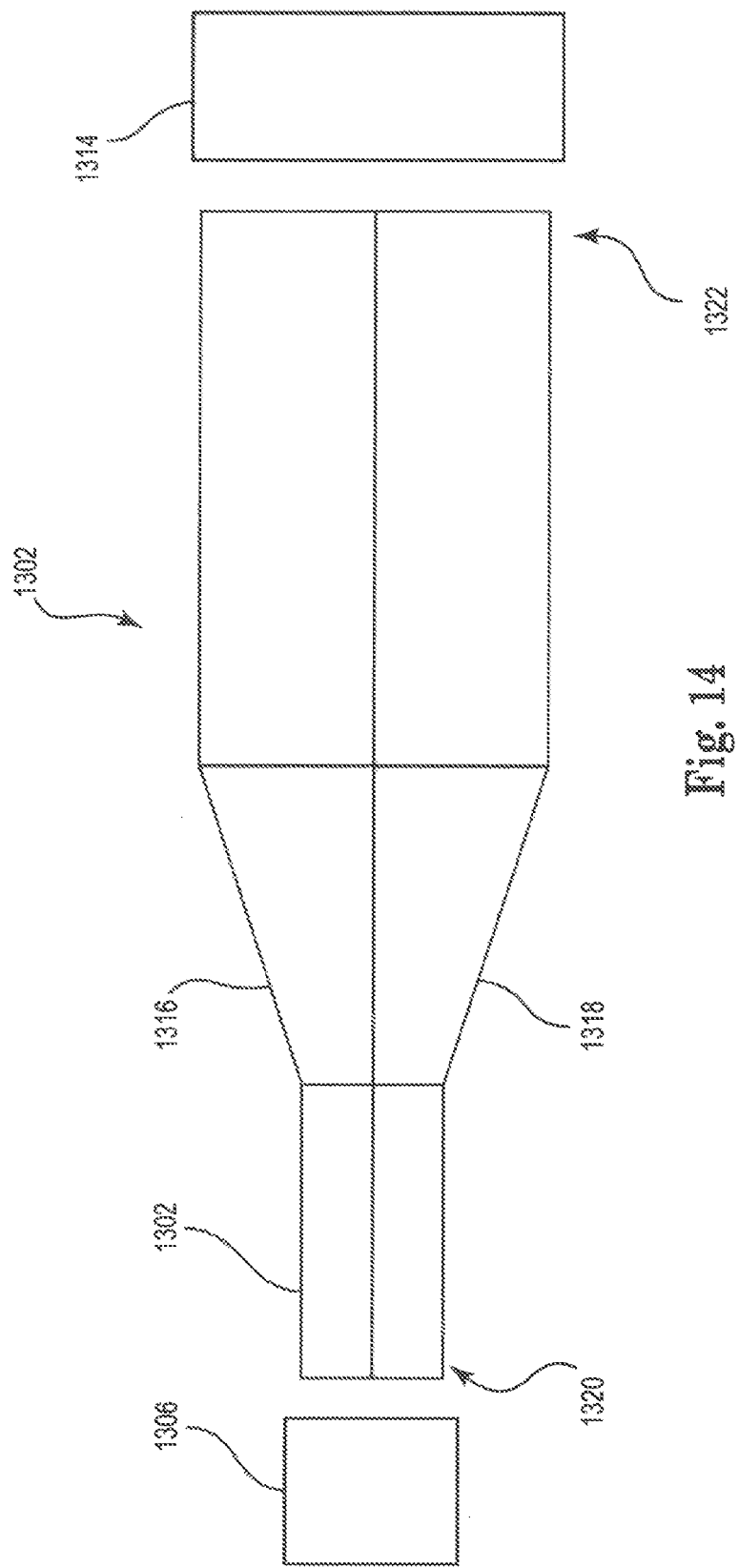
FIG. 14 illustrates the crimping funnel of FIG. 13 with the distal and proximal collars displaced from their locked position.
Figure 15:
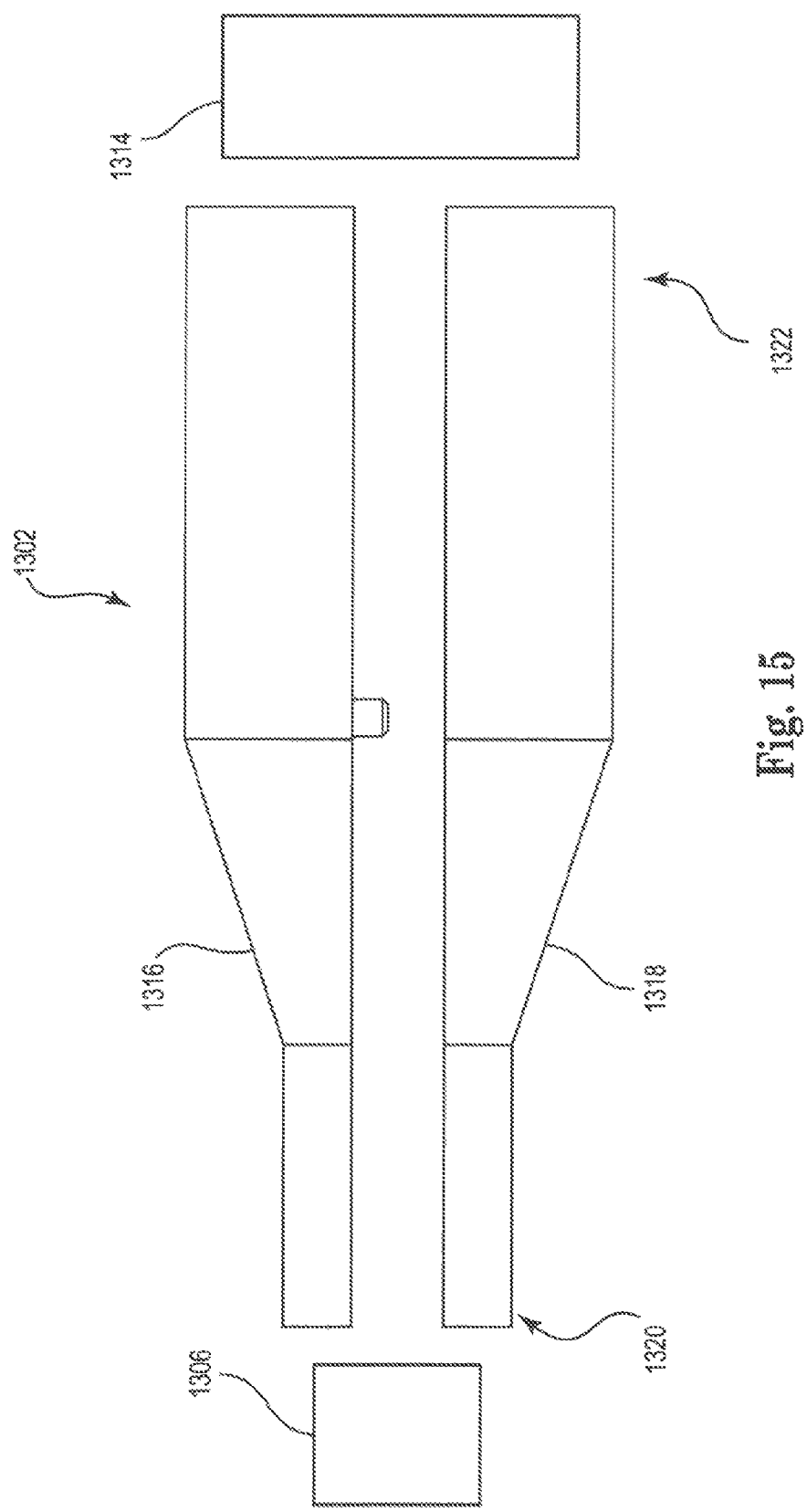
FIG. 15 illustrates the crimping funnel of FIG. 13 in its open position.

Although FIGS. 13-15 illustrate proximal funnel collar 1306 and distal funnel collar 1314 affixed to crimping funnel 1302 by the use of complementary threads, it is understood that other methods can be used to removably secure funnel collars 1306 and 1314 to crimping funnel 1302. For example, clips could be used to secure the funnel collars to crimping funnel 1302. Alternately, sliding collars could be used.

Figure 16:
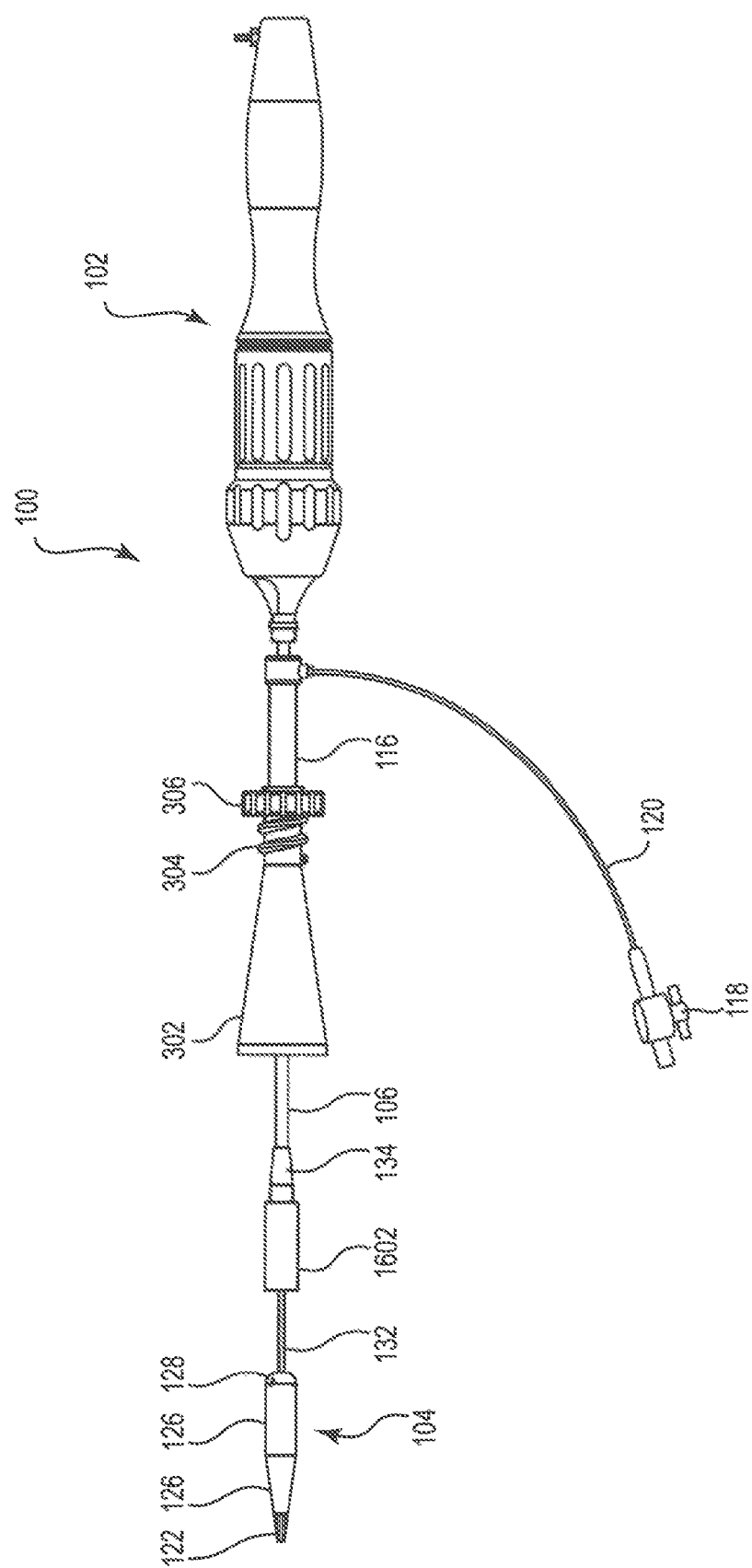
FIG. 16 illustrates a catheter assembly according to another embodiment of the present invention including accessories for crimping a prosthetic valve onto the catheter assembly.

FIG. 16 illustrates an alternate embodiment of catheter assembly 100 with crimping accessories mounted thereon. Instead of utilizing a wire loading ring to initially hold the prosthetic valve in place, the embodiment shown in FIG. 16 uses a modified valve retainer 1736, which is described in detail with reference to FIGS. 17-18, surrounded by a sleeve 1602. As with the embodiment shown in FIG. 3, the crimping accessories included with catheter 100 include a crimping funnel 302 with a split proximal end 304 and a funnel collar 306. Catheter assembly 100 is otherwise identical to the catheter assembly shown in FIGS. 1 and 3.

Figure 17:
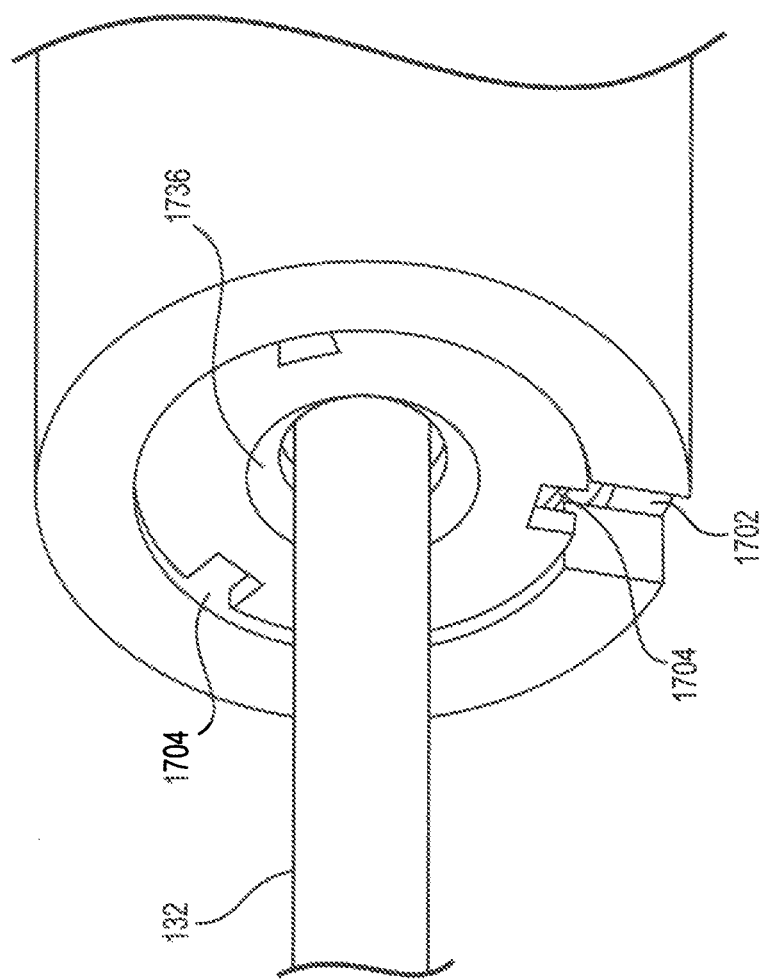
FIG. 17 is a detailed view of a valve retainer and capture sleeve according to one embodiment of the present invention.
Figure 18:
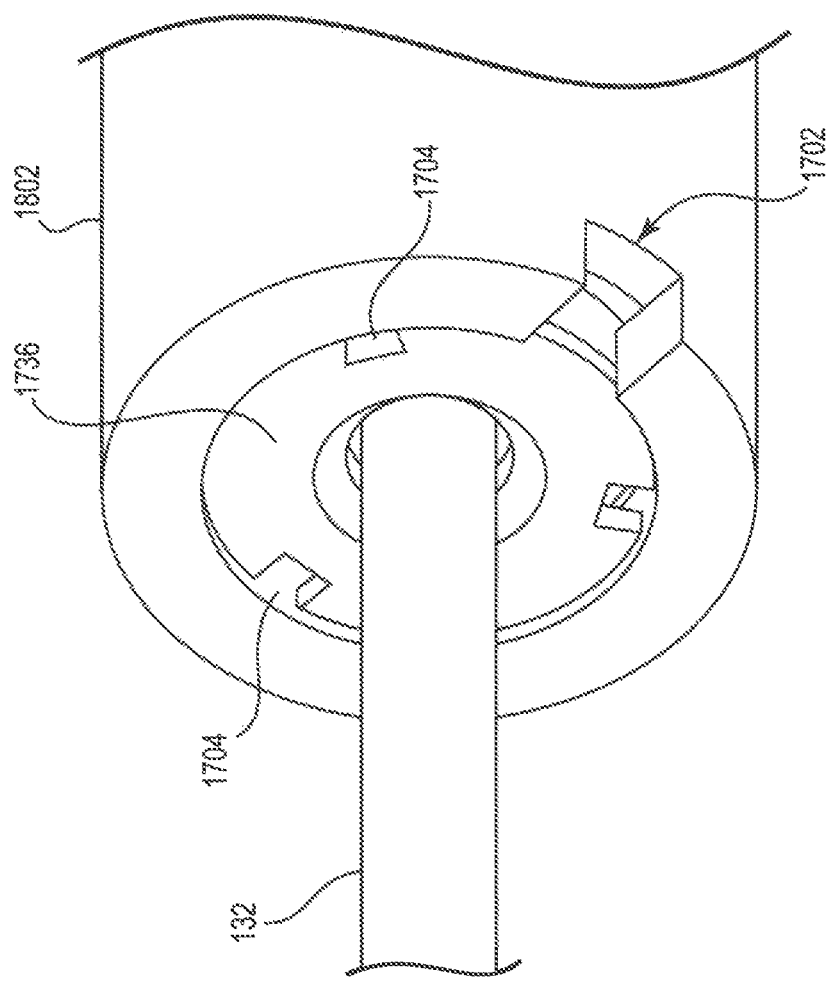
FIG. 18 illustrates the valve retainer of FIG. 16 in an alternate position.

As shown in FIG. 17, the eyelet capture sleeve 1602 is positioned around valve retainer 1736. Capture sleeve 1602 is formed with an entry notch 1702 at the distal end thereof, as shown in FIG. 17. Three retainer slots 1704 are formed in the outer perimeter of the distal end of valve retainer 1736. Retainer slots 1704 correspond to the three eyelets 208 of prosthetic valve 200, which were described in further detail above with regards to FIG. 2. Although not illustrated in FIG. 17, a circumferential channel extends around the circumference of valve retainer 1736 proximately to retainer slots 1704, much like channel 2402 shown in FIG. 24 with the respect to an alternate embodiment of a valve retainer. To load prosthetic valve 200 into valve retainer 1736, one eyelet 208 is first inserted through entry notch 702 and into a retainer slot 1704. As shown in FIG. 2, eyelets 208 are formed in generally a T-shape with the proximal end of the eyelet being wider than the face of the eyelet. Retainer slots 1704 are narrower than the proximal ends of eyelets 208. After the first eyelet has been inserted into the first retainer slot, the capture sleeve 1502 is rotated such that the first retainer slot is no longer aligned with entry notch 1702. Because the proximal end of the first eyelet 208 is wider than the retainer slot opening 1704, the first eyelet 208 is held inside the capture sleeve 1502. This process is then repeated for the second and third eyelets 208 such that all three eyelets are secured within the capture sleeve 1502 and valve retainer 1736. FIG. 18 shows valve retainer sleeve 1736 and sleeve 1602 in a position where the capture sleeve 1602 has been rotated such that the entry notch 1702 is not aligned with either of the three retainer slots 1704.

Figure 19:
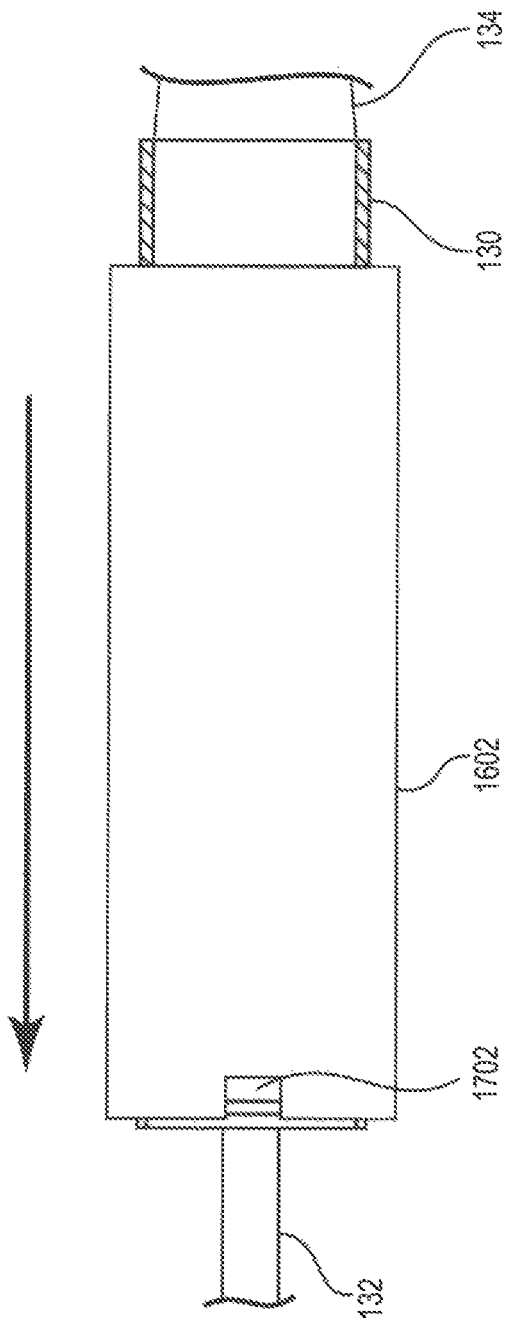
FIG. 19 illustrates removal of the capture sleeve shown in FIG. 16 from the valve retainer.

After all three eyelets 208 are secured inside the valve retainer 1736, the valve retaining sleeve 130 can be advanced underneath the capture sleeve 1602 and over valve retainer 1736, as shown in FIG. 19. After valve retaining sleeve 130 is fully advanced over the valve retainer 1736, the capture sleeve is no longer needed to retain eyelets 208 within valve retainer 1736. Capture sleeve 1602 can then be removed by sliding the sleeve distally off of the valve retaining sleeve 130. In order to remove capture sleeve 602 from the distal end of the catheter assembly 100, the capture sleeve 1602 may need to be split for removal from the catheter assembly because its internal diameter is smaller than that of the distal tip of catheter assembly 100. Capture sleeve 1602 may be pre-slit in the manner described above with reference to crimping funnel 1302. One or more collars can be used to secure the two halves of capture sleeve 1602 together prior to removal from the catheter assembly 100. As with crimping funnel 1302, the collars can be clips or sliding snap-on collars, or can be threaded to function as bolts. Alternately, capture sleeve 1602 can be formed of a single piece and can be manually cut and removed after a use.

Figure 20:
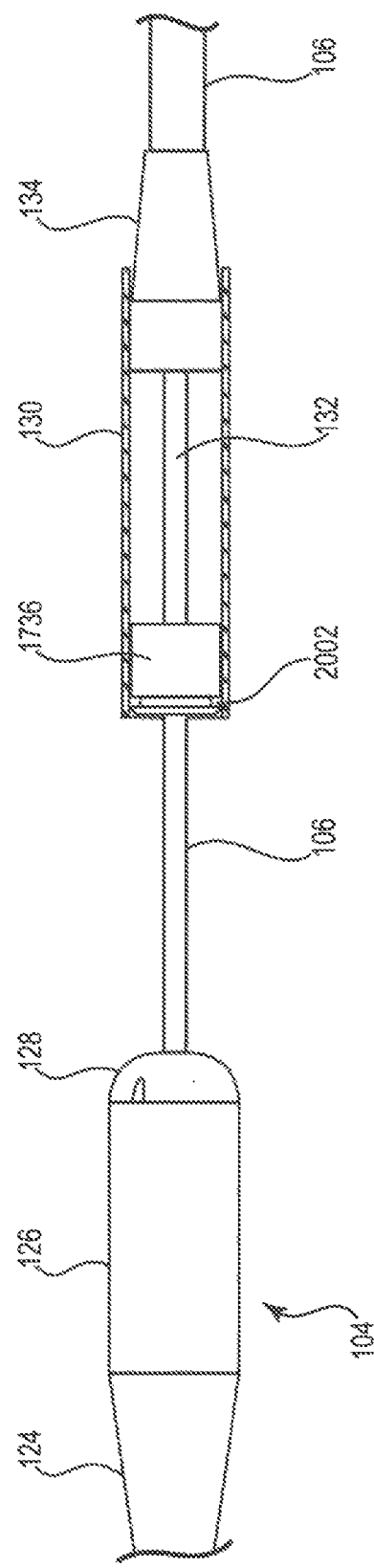
FIG. 20 illustrates the distal end of a catheter assembly according to one embodiment of the present invention prior to loading a crimping funnel onto the assembly.

After the capture sleeve 1602 is removed from the catheter assembly 100, the distal end of the catheter assembly 100 will be in the position illustrated in FIG. 20. Although prosthetic valve 200 is not depicted in FIG. 20, at this point the eyelets 208 of prosthetic valve 200 would be retained within valve retainer 1736 and the remainder of prosthetic valve 200 would be extending from the distal end of capture sleeve 130. Furthermore, although crimping funnel 302 is not shown in FIG. 20 it would at this time be positioned proximally of valve retaining sleeve 130, as shown in FIG. 16. Because the valve retainer 1736 is fixed to the intermediate shaft 132, the valve retainer serves to hold prosthetic valve assembly 200 in place as the crimping funnel is advanced over the valve assembly 200.

Figure 21:
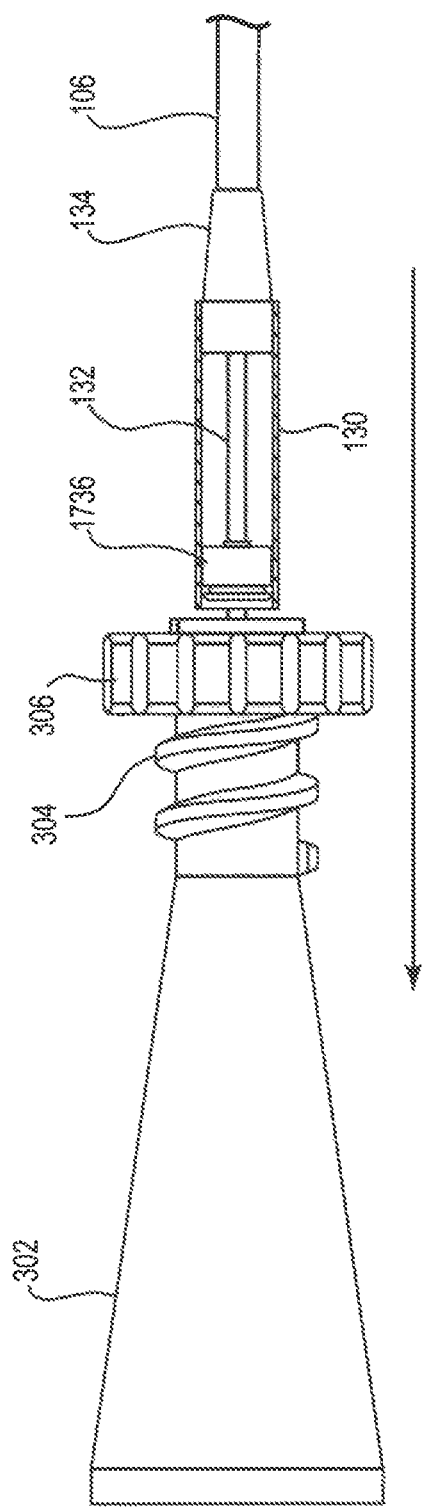
FIG. 21 illustrates the distal end of a catheter assembly according to one embodiment of the present invention with a crimping funnel loaded thereon.
Figure 22:
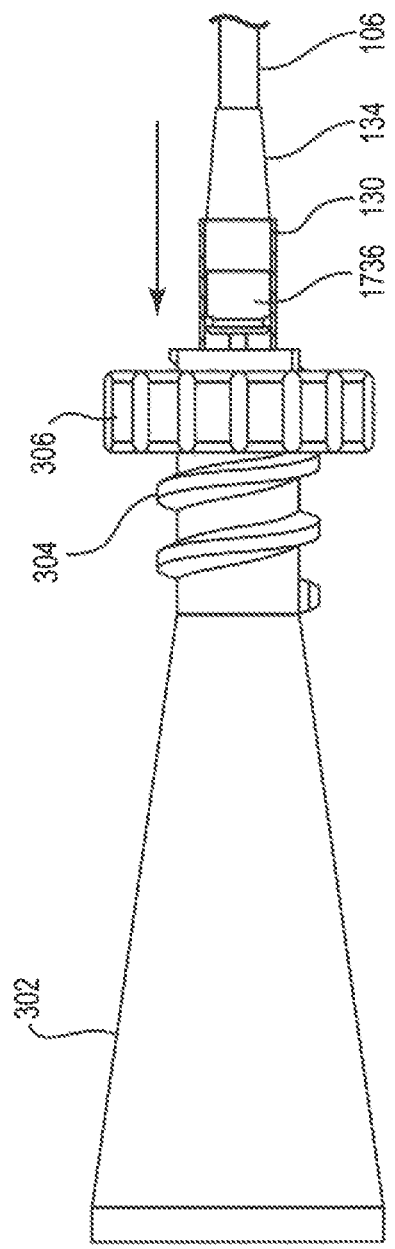
FIG. 22 illustrates a catheter assembly with crimping accessories in one stage of the crimping process. At this stage, the crimping funnel has been advanced over the prosthetic valve to crimp the valve.

Specifically, as shown in FIG. 21, the crimping funnel 302 is advanced distally while eyelets 208 of valve assembly 200 are retained within valve retainer 1736. After the prosthetic valve assembly 200 has been crimped to its delivery diameter and is housed within the split proximal end 304 of funnel 302, the outer delivery shaft is advanced over the crimped valve as shown in FIG. 22. Crimping funnel 302 is then removed from the catheter assembly in the manner described above with reference to FIGS. 7-10. Catheter assembly 100 can then be moved to its closed position by advancing introducer 116 to abut against the proximal end of support arm sleeve 126 as shown in FIG. 12.

Figure 23:
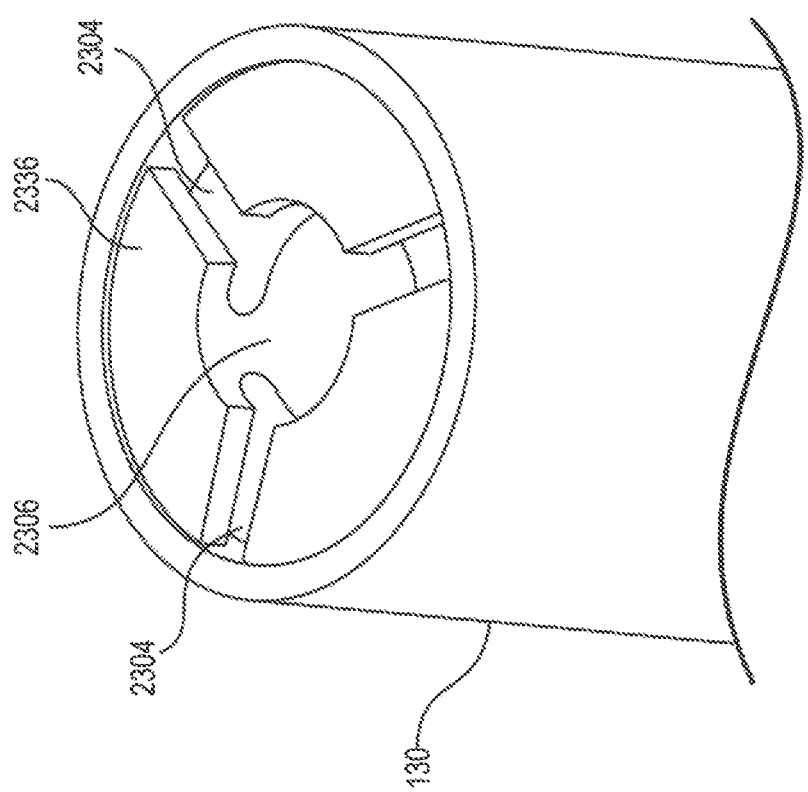
FIG. 23 illustrates a valve retainer and capture sleeve according to another embodiment of the present invention.

FIG. 23 illustrates another embodiment of a valve retainer according to the present invention. Valve retainer 2336 is configured to be operated without the need for a separate capture sleeve. Slots 2304 are opened to central lumen 2306. This configuration allows eyelets 208 to be loaded into retainer slots 2304 from the inside of central lumen 2306, thereby avoiding the need for a notch in the outer sleeve to allow introduction of the eyelets 208 into the retainer slots 2304. As a result, valve retainer 2336 can be used with valve retaining sleeve 130, eliminating the need for a separate capture sleeve and saving the user from the necessity of removing the capture sleeve after loading the valve.

Figure 24:
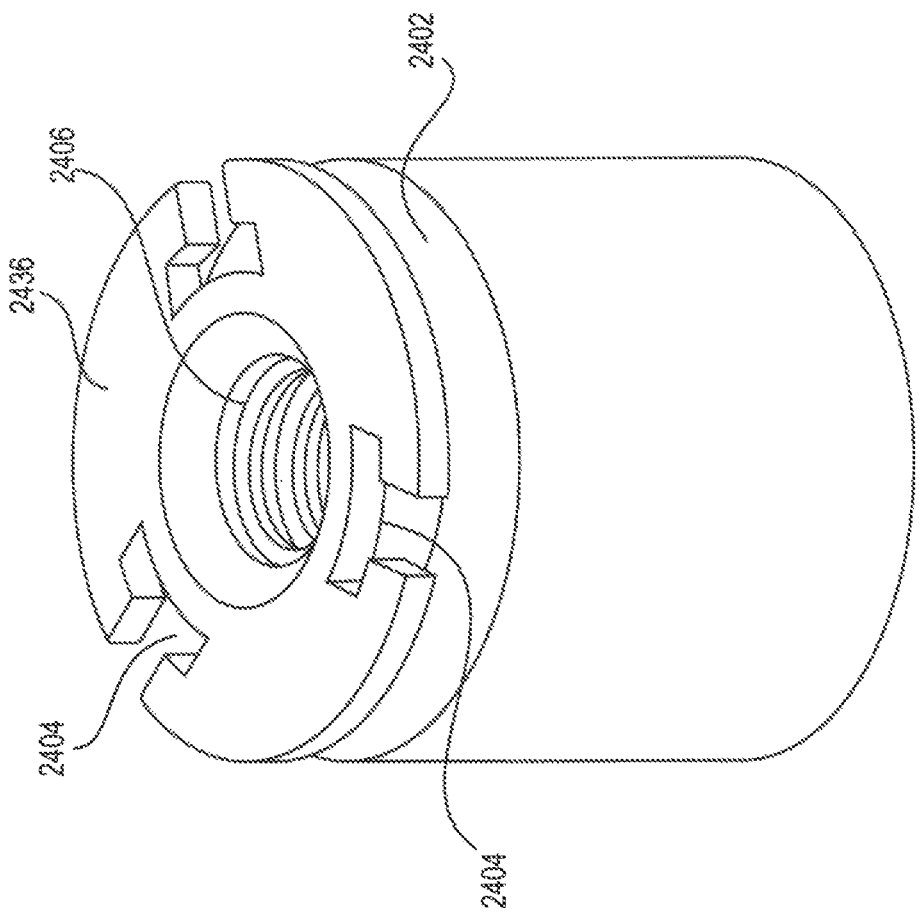
FIG. 24 illustrates a valve retainer according to yet another embodiment of the present invention.

FIG. 24 illustrates yet another embodiment of a valve retainer according to the present invention. Valve retainer 2436 has a plurality of retainer slots 2404, a circumferential channel 2402 beneath the retainer slots 2404, and a central lumen 2406 to receive intermediate delivery shaft 132. As seen in FIG. 24, the interior of retainer slots 2404 is wider than the portion of retainer slots 2404 opened to the outside of valve retainer 2436. This feature allows valve retainer 2436 to be used without the necessity of a separate capture sleeve. To load a prosthetic valve into valve retainer 2436, the ends of eyelets 208 are first inserted into the wider interior portion of slots 2404. The ends of eyelets 208 can then be moved towards the exterior of retainer slots 2404, such that the larger end of eyelets 208 are prevented from passing through the narrower portions of retainer slots 2404. Although not shown in FIG. 24, valve retainer 2436 would be encompassed by valve retaining sleeve 130 when eyelets 208 are loaded into the retainer. Therefore, eyelets 208 would be prevented from escaping the valve retainer by passing out of the retainer slots 2404 towards the exterior of valve retainer 2436. In addition, because valve 200 is preferably formed of a self expanding material, e.g., nitinol, the eyelets 208 are naturally pressed outward against valve retaining sleeve 130.

Preferably, the entire process, including securing a valve assembly to a loading ring or valve retainer, crimping the valve assembly, removing the crimping accessories from the catheter assembly, and moving the catheter assembly 100 to its closed configuration, is performed in a saline bath by a user.

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

EXAMPLES

The following paragraphs serve as examples of the above-described embodiments.

Example 1

One embodiment of the present invention provides a catheter assembly for crimping an expandable prosthesis. The catheter assembly includes a handle assembly located on the proximal end of the catheter assembly and a distal tip assembly located on the distal end of the catheter assembly. A first elongate member is provided extending from the handle assembly towards the distal tip assembly. A crimping funnel is slidably positioned over the first elongate member. The crimping funnel includes a distal end having a first diameter and a proximal end having a second diameter smaller than the first diameter. An axial split is formed in the proximal end. A first collar is provided encompassing a portion of the proximal end. The first collar is configured to hold the axial split in the proximal end together when the first collar is at a first axial location along the proximal end, and to allow the axial split in the proximal end to open when the first collar is at a second axial location along the proximal end.

The catheter assembly can include a loading ring with a plurality of loading wires secured thereto. The loading ring is positioned proximally of the crimping funnel over the first elongate member, and the loading wires extend distally from the loading ring through the interior of the funnel. The catheter assembly can include a valve retainer configured to secure a prosthetic valve to the catheter assembly. The prosthetic valve retainer is configured to prevent axial movement of the valve assembly relative to the first elongate member. The catheter assembly can also include a second collar encompassing a portion of the distal end. The axial split provided in the proximal end can extend from the proximal end of the funnel to the distal end of the funnel. The second collar is configured to hold the axial split together when the second collar is at a first axial location along the distal end, and to allow the axial split to open when the second collar is at a second axial location along the distal end.

Example 2

Another embodiment provides a method of crimping a prosthetic valve onto a catheter assembly. The method includes obtaining a catheter assembly including a first elongate member, a crimping funnel slidably positioned over the first elongate member, a valve retaining assembly positioned over the first elongate member, and a first sleeve positioned over the first elongate member. A prosthetic valve is then secured to the valve retaining assembly. The prosthetic valve is then crimped by advancing the crimping funnel in a distal direction along the first elongate member and over the first sleeve. The first sleeve is then advanced in a distal direction along the first elongate member until at least a proximal portion of the crimped prosthetic valve is encompassed by the first sleeve. Finally, the funnel is removed from the catheter assembly.

The obtained catheter assembly can also include a second sleeve positioned over the first elongate member distally of the first sleeve. The advancing step can further include retracting the second sleeve in a proximal direction along the first elongate member until the distal end of the crimped prosthetic valve is encompassed by the second sleeve.

What is claimed is:

1. A catheter assembly for crimping an expandable prosthesis, the catheter assembly comprising:
   a handle assembly located on the proximal end of the catheter assembly;
   a distal tip assembly located on the distal end of the catheter assembly and having a distal tip assembly diameter;
   a first elongate member, the first elongate member extending from the handle assembly towards the distal tip assembly; and a crimping funnel slidably positioned over the first elongate member and the distal tip assembly, the crimping funnel comprising:
  a distal end having a first diameter;
  a proximal end having a second diameter smaller than the first diameter, the proximal end having an axial split, wherein the second diameter is less than the distal tip assembly diameter; and
  a first collar encompassing a portion of the proximal end, wherein the first collar is configured to hold the axial split in the proximal end together when the first collar is at a first axial location along the proximal end, and wherein the first collar is configured to allow the axial split in the proximal end to open when the first collar is at a second axial location along the proximal end,
wherein the axial split allows the second diameter of the proximal end of the crimping funnel to increase to a diameter larger than the distal tip assembly, when the first collar is in the second axial location,
wherein the crimping funnel is positioned over the first elongate member such that the first elongate member is disposed within the proximal end of the crimping funnel and the distal tip assembly is disposed within or distal of the distal end of the crimping funnel such that the distal tip assembly is disposed distal of the first diameter with the first collar at the first axial location.

2. A catheter assembly according to claim 1, further comprising a loading ring with a plurality of loading wires secured thereto, wherein the loading ring is positioned proximally of the crimping funnel over the first elongate member, and wherein the loading wires extend distally from the loading ring through an interior of the funnel.

3. A catheter assembly according to claim 1, further comprising a valve retainer configured to secure a prosthetic valve to the catheter assembly, wherein the prosthetic valve retainer is configured to prevent axial movement of the valve assembly relative to the first elongate member.

4. A catheter assembly according to claim 1, further comprising a second collar encompassing a portion of the distal end, wherein the second collar is separate from the first collar such that the second collar moves independently of the first collar, wherein the axial split extends from the proximal end of the funnel to the distal end of the funnel, and wherein the second collar is configured to hold the axial split together when the second collar is at a first axial location along the distal end, and wherein the second collar is configured to allow the axial split to open when the second collar is at a second axial location along the distal end.

5. A catheter assembly according to claim 1, wherein the first collar is mounted to the crimping funnel.

6. A catheter assembly according to claim 1, wherein the first collar is rotatably mounted to the crimping funnel.

7. A catheter assembly according to claim 6, wherein rotating the first collar causes the first collar to move between the first axial location and the second axial location.

8. A catheter assembly according to claim 1, wherein the crimping funnel is configured to reduce the diameter of a prosthetic valve passing therethrough.

9. A method of crimping a prosthetic valve onto a catheter assembly, the method comprising:
  securing a prosthetic valve to a valve retaining assembly of a catheter assembly, the catheter assembly further including:
  a first elongate member;
  a crimping funnel slidably positioned over the first elongate member; and
  a first sleeve positioned over the first elongate member;
  wherein the valve retaining assembly is positioned over the first elongate member;
  crimping the prosthetic valve by advancing the crimping funnel in a distal direction along the first elongate member and over the first sleeve;
  advancing the first sleeve in a distal direction along the first elongate member until at least a proximal portion of the crimped prosthetic valve is encompassed by the first sleeve; and
  removing the funnel from the catheter assembly.

10. The method of claim 9, wherein the catheter assembly further includes a second sleeve positioned over the first elongate member distally of the first sleeve, wherein the advancing step further includes retracting the second sleeve in a proximal direction along the first elongate member until the distal end of the crimped prosthetic valve is encompassed by the second sleeve.

* * * * *